US009687345B2

(12) United States Patent
Rabito et al.

(10) Patent No.: US 9,687,345 B2
(45) Date of Patent: Jun. 27, 2017

(54) PROSTHESIS, DELIVERY DEVICE AND METHODS OF USE

(71) Applicant: Edwards Lifesciences CardiAQ LLC, Irvine, CA (US)

(72) Inventors: Glen T. Rabito, Lake Forest, CA (US); Julio Cesar Sanchez, Garden Grove, CA (US); Arshad Quadri, West Hartford, CT (US); J. Brent Ratz, Winchester, MA (US); Luca Pesce, Huntington Beach, CA (US); Yen Liao, Arlington, VA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 152 days.

(21) Appl. No.: 14/724,355

(22) Filed: May 28, 2015

(65) Prior Publication Data

US 2015/0342736 A1    Dec. 3, 2015

Related U.S. Application Data

(60) Provisional application No. 62/004,610, filed on May 29, 2014.

(51) Int. Cl.
*A61F 2/24* (2006.01)
*A61F 2/95* (2013.01)
*A61F 2/966* (2013.01)

(52) U.S. Cl.
CPC .......... *A61F 2/2439* (2013.01); *A61F 2/2427* (2013.01); *A61F 2/2436* (2013.01); *A61F 2/95* (2013.01); *A61F 2002/9665* (2013.01)

(58) Field of Classification Search
CPC .................. A61F 2/2436; A61F 2/2439; A61F 2002/9665; A61F 2220/0008; A61F 2220/0033; A61F 2/95
USPC ................................................ 623/1.11, 2.11
See application file for complete search history.

(56) References Cited

U.S. PATENT DOCUMENTS

| 4,378,224 | A | 3/1983 | Nimni et al. |
| 4,553,974 | A | 11/1985 | Dewanjee |
| 4,573,470 | A | 3/1986 | Samson et al. |
| 4,582,181 | A | 4/1986 | Samson |

(Continued)

FOREIGN PATENT DOCUMENTS

| DE | 19907646 A1 | 8/2000 |
| DE | 202010000329 U1 | 5/2010 |

(Continued)

OTHER PUBLICATIONS

Int'l. Search Report issued in PCT/US2015/032978, Completed Sep. 1, 2015.

*Primary Examiner* — Katherine M Shi
(74) *Attorney, Agent, or Firm* — Knobbe Martens Olson & Bear LLP (57) ABSTRACT

Disclosed herein are embodiments of a prosthesis and delivery device, as well as methods of use. The delivery device can be composed of an inner retention assembly configured to carry an expandable prosthesis to an in situ target location. The inner retention assembly can slide within an outer elongate hollow member which can cover the expandable prosthesis. The outer elongate hollow member can further be longitudinally collapsed into a receiving member located at the distal end of the outer elongate hollow member.

11 Claims, 7 Drawing Sheets

(56) References Cited

U.S. PATENT DOCUMENTS

| | | |
|---|---|---|
| 4,605,002 A | 8/1986 | Rebuffat |
| 4,647,283 A | 3/1987 | Carpentier et al. |
| 4,648,881 A | 3/1987 | Carpentier et al. |
| 4,753,652 A | 6/1988 | Langer et al. |
| 4,944,740 A | 7/1990 | Buchbinder et al. |
| 5,059,186 A | 10/1991 | Yamamoto et al. |
| 5,125,895 A | 6/1992 | Buchbinder et al. |
| 5,188,636 A | 2/1993 | Fedotov |
| 5,304,184 A | 4/1994 | Hathaway et al. |
| 5,306,234 A | 4/1994 | Johnson |
| 5,318,587 A | 6/1994 | Davey |
| 5,320,632 A | 6/1994 | Heidmueller |
| 5,350,361 A | 9/1994 | Tsukashima et al. |
| 5,364,408 A | 11/1994 | Gordon |
| 5,368,601 A | 11/1994 | Sauer et al. |
| 5,370,685 A | 12/1994 | Stevens |
| 5,374,275 A | 12/1994 | Bradley et al. |
| 5,403,329 A | 4/1995 | Hinchcliffe |
| 5,417,699 A | 5/1995 | Klein et al. |
| 5,417,700 A | 5/1995 | Egan |
| 5,425,737 A | 6/1995 | Burbank et al. |
| 5,431,666 A | 7/1995 | Sauer et al. |
| 5,458,572 A | 10/1995 | Campbell et al. |
| 5,527,322 A | 6/1996 | Klein et al. |
| 5,534,007 A * | 7/1996 | St. Germain ............. A61F 2/95 606/191 |
| 5,537,322 A | 7/1996 | Denz et al. |
| 5,545,214 A | 8/1996 | Stevens |
| 5,571,215 A | 11/1996 | Sterman et al. |
| 5,713,951 A | 2/1998 | Garrison et al. |
| 5,718,725 A | 2/1998 | Sterman et al. |
| 5,792,152 A | 8/1998 | Klein et al. |
| 5,792,172 A | 8/1998 | Fischell et al. |
| 5,797,960 A | 8/1998 | Stevens et al. |
| 5,810,850 A | 9/1998 | Hathaway et al. |
| 5,820,631 A | 10/1998 | Nobles |
| 5,860,990 A | 1/1999 | Nobles et al. |
| 5,891,159 A | 4/1999 | Sherman et al. |
| 5,924,424 A | 7/1999 | Stevens et al. |
| 5,968,068 A | 10/1999 | Dehdashtian et al. |
| 5,972,005 A | 10/1999 | Stalker et al. |
| 5,972,030 A | 10/1999 | Garrison et al. |
| 6,001,056 A | 12/1999 | Jassawalla et al. |
| 6,004,328 A * | 12/1999 | Solar ............. A61F 2/95 604/271 |
| 6,013,092 A | 1/2000 | Dehdashtian et al. |
| 6,033,378 A | 3/2000 | Lundquist et al. |
| 6,071,273 A | 6/2000 | Euteneuer et al. |
| 6,083,257 A | 7/2000 | Taylor et al. |
| 6,106,540 A | 8/2000 | White et al. |
| 6,117,144 A | 9/2000 | Nobles et al. |
| 6,143,004 A | 11/2000 | Davis et al. |
| 6,146,325 A | 11/2000 | Lewis et al. |
| 6,174,327 B1 * | 1/2001 | Mertens ............. A61F 2/958 606/108 |
| 6,206,893 B1 | 3/2001 | Klein et al. |
| 6,231,563 B1 | 5/2001 | White et al. |
| 6,245,079 B1 | 6/2001 | Nobles et al. |
| 6,251,092 B1 | 6/2001 | Qin et al. |
| 6,269,819 B1 | 8/2001 | Oz et al. |
| 6,346,074 B1 | 2/2002 | Roth |
| 6,358,258 B1 | 3/2002 | Arcia et al. |
| 6,379,372 B1 | 4/2002 | Dehdashtian et al. |
| 6,425,916 B1 | 7/2002 | Garrison et al. |
| 6,454,777 B1 | 9/2002 | Green |
| 6,506,339 B1 | 1/2003 | Girardot et al. |
| 6,517,553 B2 | 2/2003 | Klein et al. |
| 6,540,782 B1 | 4/2003 | Snyders |
| 6,551,331 B2 | 4/2003 | Nobles et al. |
| 6,558,418 B2 | 5/2003 | Carpentier et al. |
| 6,562,052 B2 | 5/2003 | Nobles et al. |
| 6,591,472 B1 | 7/2003 | Noone et al. |
| 6,626,917 B1 | 9/2003 | Craig |
| 6,679,268 B2 | 1/2004 | Stevens et al. |
| 6,682,558 B2 | 1/2004 | Tu et al. |
| 6,702,255 B2 | 3/2004 | Dehdashtian |
| 6,716,207 B2 | 4/2004 | Farnholtz |
| 6,726,717 B2 | 4/2004 | Alfieri et al. |
| 6,730,118 B2 | 5/2004 | Spenser et al. |
| 6,733,509 B2 | 5/2004 | Nobles et al. |
| 6,743,239 B1 | 6/2004 | Kuehn et al. |
| 6,746,471 B2 | 6/2004 | Mortier et al. |
| 6,749,630 B2 | 6/2004 | McCarthy et al. |
| 6,805,710 B2 | 10/2004 | Bolling et al. |
| 6,821,297 B2 | 11/2004 | Snyders |
| 6,830,584 B1 | 12/2004 | Seguin |
| 6,858,039 B2 | 2/2005 | McCarthy |
| 6,890,330 B2 | 5/2005 | Streeter et al. |
| 6,893,460 B2 | 5/2005 | Spenser et al. |
| 6,899,704 B2 | 5/2005 | Sterman et al. |
| 6,908,481 B2 | 6/2005 | Cribier |
| 6,911,034 B2 | 6/2005 | Nobles et al. |
| 6,978,176 B2 | 12/2005 | Lattouf |
| 6,991,642 B2 * | 1/2006 | Petersen ............. A61F 2/013 606/200 |
| 6,994,666 B2 | 2/2006 | Shannon et al. |
| 7,004,952 B2 | 2/2006 | Nobles et al. |
| 7,078,163 B2 | 7/2006 | Torrianni |
| 7,090,686 B2 | 8/2006 | Nobles et al. |
| 7,100,614 B2 | 9/2006 | Stevens et al. |
| 7,160,322 B2 | 1/2007 | Gabbay |
| 7,201,772 B2 | 4/2007 | Schwammenthal et al. |
| 7,273,468 B2 | 9/2007 | Bedell |
| 7,276,078 B2 | 10/2007 | Spenser et al. |
| 7,294,148 B2 | 11/2007 | McCarthy |
| 7,323,004 B2 | 1/2008 | Parihar |
| 7,373,207 B2 | 5/2008 | Lattouf |
| 7,377,926 B2 | 5/2008 | Topper et al. |
| 7,399,315 B2 | 7/2008 | Iobbi |
| 7,510,572 B2 | 3/2009 | Gabbay |
| 7,513,908 B2 | 4/2009 | Lattouf |
| 7,534,260 B2 | 5/2009 | Lattouf |
| 7,569,062 B1 | 8/2009 | Kuehn et al. |
| 7,604,650 B2 | 10/2009 | Bergheim |
| 7,611,535 B2 | 11/2009 | Woolfson et al. |
| 7,648,528 B2 | 1/2010 | Styrc |
| 7,780,723 B2 | 8/2010 | Taylor |
| 7,803,167 B2 | 9/2010 | Nobles et al. |
| 7,803,185 B2 | 9/2010 | Gabbay |
| 7,905,892 B2 | 3/2011 | Nobles et al. |
| 8,075,606 B2 | 12/2011 | Dorn |
| 8,182,530 B2 | 5/2012 | Huber |
| 2001/0001812 A1 | 5/2001 | Valley et al. |
| 2001/0025643 A1 | 10/2001 | Foley |
| 2002/0032481 A1 | 3/2002 | Gabbay |
| 2002/0123802 A1 | 9/2002 | Snyders |
| 2002/0128707 A1 | 9/2002 | Kavteladze et al. |
| 2002/0151970 A1 | 10/2002 | Garrison et al. |
| 2002/0165571 A1 | 11/2002 | Hebert et al. |
| 2002/0183839 A1 | 12/2002 | Garrison et al. |
| 2003/0040792 A1 | 2/2003 | Gabbay |
| 2003/0109924 A1 | 6/2003 | Cribier |
| 2003/0114913 A1 | 6/2003 | Spenser et al. |
| 2003/0130571 A1 | 7/2003 | Lattouf |
| 2003/0163194 A1 | 8/2003 | Quijano et al. |
| 2003/0199975 A1 | 10/2003 | Gabbay |
| 2004/0034411 A1 | 2/2004 | Quijano et al. |
| 2004/0039436 A1 | 2/2004 | Spenser et al. |
| 2004/0116897 A1 | 6/2004 | Aboul-Hosn |
| 2004/0162608 A1 | 8/2004 | Haverich |
| 2004/0215139 A1 | 10/2004 | Cohen |
| 2004/0260309 A1 | 12/2004 | Packard |
| 2005/0043791 A1 | 2/2005 | McCarthy et al. |
| 2005/0049698 A1 | 3/2005 | Bolling et al. |
| 2005/0070844 A1 | 3/2005 | Chow et al. |
| 2005/0075729 A1 | 4/2005 | Nguyen et al. |
| 2005/0131533 A1 | 6/2005 | Alfieri et al. |
| 2005/0137695 A1 | 6/2005 | Salahieh et al. |
| 2005/0148997 A1 | 7/2005 | Valley et al. |
| 2005/0209671 A1 | 9/2005 | Ton et al. |
| 2005/0222603 A1 * | 10/2005 | Andreas ............. A61F 2/958 606/194 |
| 2005/0228407 A1 | 10/2005 | Nobles et al. |
| 2005/0240200 A1 | 10/2005 | Bergheim |

(56) References Cited

U.S. PATENT DOCUMENTS

| | | |
|---|---|---|
| 2005/0251251 A1 | 11/2005 | Cribier |
| 2005/0271844 A1 | 12/2005 | Mapes et al. |
| 2006/0004439 A1 | 1/2006 | Spenser et al. |
| 2006/0036265 A1 | 2/2006 | Dant |
| 2006/0036313 A1 | 2/2006 | Vassiliades |
| 2006/0142848 A1 | 6/2006 | Gabbay |
| 2006/0178675 A1 | 8/2006 | Hamman |
| 2006/0195120 A1 | 8/2006 | Nobles et al. |
| 2006/0212056 A1 | 9/2006 | Salvadori et al. |
| 2006/0217803 A1 | 9/2006 | Ingle et al. |
| 2006/0271064 A1 | 11/2006 | Agnew |
| 2006/0276889 A1 | 12/2006 | Chambers et al. |
| 2006/0282102 A1 | 12/2006 | Nobles et al. |
| 2006/0282152 A1* | 12/2006 | Beyerlein ............ A61F 2/966 623/1.11 |
| 2006/0293745 A1 | 12/2006 | Carpentier et al. |
| 2007/0005131 A1 | 1/2007 | Taylor |
| 2007/0010829 A1 | 1/2007 | Nobles et al. |
| 2007/0021828 A1 | 1/2007 | Krolik et al. |
| 2007/0043385 A1 | 2/2007 | Nobles et al. |
| 2007/0112422 A1 | 5/2007 | Dehdashtian |
| 2007/0123979 A1 | 5/2007 | Perier et al. |
| 2007/0149987 A1 | 6/2007 | Wellman et al. |
| 2007/0203479 A1 | 8/2007 | Auth et al. |
| 2007/0203506 A1 | 8/2007 | Sibbitt et al. |
| 2007/0208550 A1 | 9/2007 | Cao et al. |
| 2007/0276413 A1 | 11/2007 | Nobles |
| 2007/0276414 A1 | 11/2007 | Nobles |
| 2008/0004597 A1 | 1/2008 | Lattouf et al. |
| 2008/0033459 A1 | 2/2008 | Shafi et al. |
| 2008/0058839 A1 | 3/2008 | Nobles et al. |
| 2008/0071362 A1 | 3/2008 | Tuval et al. |
| 2008/0188873 A1 | 8/2008 | Speziali |
| 2008/0269786 A1 | 10/2008 | Nobles et al. |
| 2009/0099578 A1 | 4/2009 | Heneveld et al. |
| 2009/0240264 A1 | 9/2009 | Tuval et al. |
| 2009/0287182 A1 | 11/2009 | Bishop et al. |
| 2009/0287183 A1 | 11/2009 | Bishop et al. |
| 2010/0030242 A1 | 2/2010 | Nobles et al. |
| 2010/0069852 A1 | 3/2010 | Kelley |

FOREIGN PATENT DOCUMENTS

| | | |
|---|---|---|
| EP | 0815805 A2 | 1/1998 |
| EP | 941698 A1 | 9/1999 |
| EP | 1 356 793 A2 | 10/2003 |
| EP | 1447111 A1 | 8/2004 |
| EP | 1570790 A2 | 9/2005 |
| EP | 2114318 A1 | 11/2009 |
| EP | 2120794 A1 | 11/2009 |
| GB | 2335146 A | 9/1999 |
| WO | 94/13211 A1 | 6/1994 |
| WO | 95/03742 A1 | 2/1995 |
| WO | 95/13021 A1 | 5/1995 |
| WO | 96/40347 A1 | 12/1996 |
| WO | 99/03904 A1 | 1/1999 |
| WO | 01/08050 A1 | 2/2001 |
| WO | 01/26724 A2 | 4/2001 |
| WO | 2004/019825 A1 | 3/2004 |
| WO | 2005/034801 A2 | 4/2005 |
| WO | 2005/102015 | 11/2005 |
| WO | 2005/107650 A2 | 11/2005 |
| WO | 2006/019798 A1 | 2/2006 |
| WO | 2006/023676 A1 | 3/2006 |
| WO | 2006/041505 A1 | 4/2006 |
| WO | WO2006041505 | 4/2006 |
| WO | 2006/127765 A1 | 11/2006 |
| WO | 2006/138173 A2 | 12/2006 |
| WO | 2007/002920 A2 | 1/2007 |
| WO | 2008/058519 A1 | 5/2008 |
| WO | 2011/017150 A2 | 2/2011 |
| WO | 2011/081997 A1 | 7/2011 |
| WO | 2012/095455 A2 | 7/2012 |

* cited by examiner

PROSTHESIS, DELIVERY DEVICE AND METHODS OF USE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

Certain embodiments disclosed herein relate generally to prostheses for implantation within a lumen or body cavity and delivery devices for a prosthesis. In particular, the prostheses and delivery devices relate in some embodiments to replacement heart valves, such as replacement mitral heart valves.

Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example delivering a replacement heart valve to the mitral valve, can also be challenging. Obtaining access to perform procedures in the heart or in other anatomical locations may require delivery of devices percutaneously through tortuous vasculature or through open or semi-open surgical procedures. The ability to control the deployment of the prosthesis at the desired location can also be challenging.

SUMMARY

Embodiments of the present disclosure are directed to a prosthesis, such as but not limited to a replacement heart valve. Further embodiments are directed to delivery systems, devices and/or methods of use to deliver and/or controllably deploy a prosthesis, such as but not limited to a replacement heart valve, to a desired location within the body. In some embodiments, a replacement heart valve and methods for delivering a replacement heart valve to a native heart valve, such as a mitral valve, are provided.

It should be appreciated that access to certain anatomical features can be difficult due to limited anatomical space to maneuver surgical tools and instruments. This can be particularly true for access to the mitral valve via transfemoral, transatrial and transapical approaches. Accordingly, it is generally advantageous to reduce the form factor for these surgical tools and instruments to more efficiently maneuver the tools and instruments within the limited anatomical space. The delivery devices described herein utilize an outer elongate hollow member which compresses or collapses to expose the prosthesis contained therein. Accordingly, the delivery devices can have a significantly reduced length as compared to delivery devices which utilize a rigid capsule assembly. Rigid capsule delivery devices can often require a straight, rigid length which is about twice as long as the prosthesis as the entirety of the rigid capsule, which has a length about equal to the prosthesis, must be fully withdrawn over the prosthesis to expose the prosthesis. In contrast, the outer elongate hollow member of the devices described herein can collapse and reduce in length to expose the prosthesis, thereby greatly reducing the length of the delivery device.

Disclosed herein are embodiments of a delivery system for controlled deployment of an expandable prosthesis, the delivery system comprising an inner retention assembly comprising an inner elongate member having a proximal end and a distal end configured to carry the expandable prosthesis to an in situ target location, wherein the inner retention assembly is configured to radially restrain a first end of the expandable prosthesis when the expandable prosthesis is mounted over the inner elongate member with the second end of the expandable prosthesis positioned proximally of the first end, an outer elongate hollow member having a proximal end and a distal end that is slidable over the inner retention assembly, the outer elongate hollow member configured to cover the first and second ends of the expandable prosthesis when the expandable prosthesis is mounted over the inner elongate member, and a receiving member provided at the distal end of the outer elongate hollow member, wherein the distal end of the outer elongate hollow member is positioned within the receiving member and the proximal end of the outer elongate hollow member is spaced proximally away from the receiving member, wherein the outer elongate hollow member is moveable in a distal direction relative to the inner retention assembly to uncover at least the second end of the expandable prosthesis when the expandable prosthesis is mounted over the inner elongate member, wherein distal movement of the outer elongate hollow member relative to the inner retention assembly causes longitudinal collapse of at least a portion of the outer elongate hollow member into the receiving member.

In some embodiments, the inner retention assembly can comprise an inner retention ring at the distal end of the inner elongate member configured to engage the first end of the expandable prosthesis. In some embodiments, the inner retention assembly can further comprise an outer retention ring configured to cover the inner retention ring when the inner retention ring engages the first end of the expandable prosthesis.

In some embodiments, the receiving member can comprise a nose cone. In some embodiments, the delivery system can further comprise a nose cone shaft slidable within the inner elongate member, wherein the nose cone is connected to a distal end of the nose cone shaft.

In some embodiments, the delivery device can further comprise a plurality of pull wires connected to a proximal portion of the outer member and configured pull the outer member distally into the receiving member. In some embodiments, the pull wires can extend through a curved path within the receiving member.

In some embodiments, the delivery device can further comprise a squash plate configured to cause longitudinal collapse of the outer member. In some embodiments, the delivery device can further comprise a compression shaft slidable within the inner retention assembly, wherein the squash plate is connected to a distal end of the compression shaft.

In some embodiments, the outer elongate hollow member can comprise a collapsible polymer sheath. In some embodiments, the delivery device can further comprise an expandable prosthesis having a first end radially restrained by the inner retention assembly and wherein the first end and the second end of the expandable prosthesis are covered by the outer elongate hollow member.

BRIEF DESCRIPTION OF THE DRAWINGS

These and other features, aspects and advantages are described below with reference to the drawings, which are intended to illustrate but not to limit the invention.

DETAILED DESCRIPTION

The present specification and drawings provide aspects and features of the disclosure in the context of several embodiments of replacement heart valves, delivery devices and methods that are configured for use in the vasculature of a patient, such as for replacement of natural heart valves in a patient. The devices, systems, and methods described herein can be used to transapically deliver a replacement heart valve to a mitral valve location. However, while these embodiments may be discussed in connection with replacing specific valves such as the patient's aortic or mitral valve, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery device, etc. should not be taken as limiting, and features of any one embodiment discussed herein can be combined with features of other embodiments as desired and when appropriate.

The implant or prosthesis can take any number of different forms. Example designs for a prosthesis are described in U.S. Pat. Nos. 8,403,983, 8,414,644, and 8,652,203; U.S. Patent Publication Nos. 2011/0313515 and US 2012/0215303; U.S. application Ser. Nos. 14/197,590, 14/197,639 and 14/197,690, all applications filed Mar. 5, 2014, the entirety of these patents, publications and applications are hereby incorporated by reference and made a part of this specification. In some embodiments, the longitudinal axis of the prosthesis, which runs between the first and second ends of the prosthesis, can be parallel to and/or concentric with the longitudinal axis of one or more shafts and/or sheaths of the delivery systems described herein. Further, while specific embodiments of delivery systems are disclosed herein, they can be used in conjunction with delivery devices described in U.S. patent application Ser. Nos. 14/716,507 and 14/628,034, the entirety of these applications hereby incorporated by reference and made a part of this specification.

Figure 1:
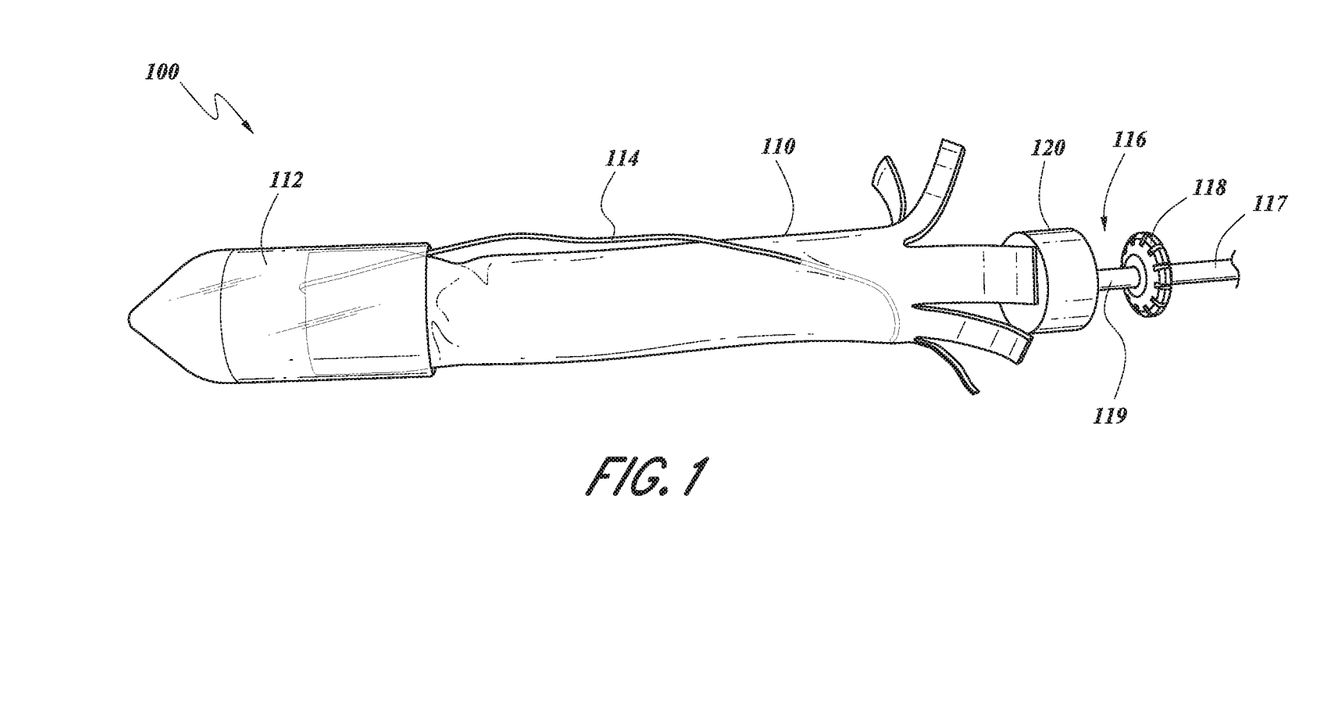
FIG. 1 shows a side elevation view of an embodiment of a delivery system having pull wires.

With reference first to the embodiment shown in FIG. 1 which illustrates a delivery device or system 100, the delivery system 100 can include an outer elongate hollow member 110 such as a sheath, a receiving member 112 such as a nose cone, and one or more pull wires 114. As shown in the illustrated embodiment, the outer elongate hollow member 110 can have a distal end being positioned at least partially within the receiving member 112 (toward the left in FIG. 1) and a proximal end being spaced away from the receiving member 112 (toward the right in FIG. 1). As used to describe the components of the delivery system, "proximal" refers to a location of the component that is closer to the operator, and "distal" refers to a location of the component that is further from the operator. Based on the orientation of these figures, "proximal" would refer to a location to the right of the figures whereas "distal" would refer to a location to the left of the figures. The one or more pull wires 114 can be attached to at least a portion of the outer elongate hollow member 110. Preferably, the one or more pull wires 114 are attached to a proximal portion of the outer elongate hollow member 110. In some embodiments, the one or more pull wires 114 are attached proximate to or at the proximal end of the outer elongate hollow member 110. As will be described in further detail below, the one or more pull wires 114 can be used to collapse the outer elongate hollow member 110 to uncover at least part of a prosthesis, such as an expandable prosthesis, engaged on the delivery system 100.

With continued reference to the embodiment shown in FIG. 1, the delivery system 100 can include an inner retention assembly 116 designed to carry the expandable prosthesis to an in situ target location. The inner retention assembly 116 can be designed to radially restrain a first end of the expandable prosthesis when the expandable prosthesis is mounted thereon with a second end of the expandable prosthesis extending proximally therefrom. In some embodiments, the inner retention assembly 116 can include an inner retention shaft 117, having a proximal and distal end, over which the expandable prosthesis can be mounted. In some embodiments, the inner retention shaft 117 can be used to carry and/or transport the expandable prosthesis to the in situ target location. As shown in the illustrated embodiment, the inner retention assembly 116 can include an inner retention member 118, such as an inner retention ring, attached to a distal end of the inner retention shaft 117. The inner retention member 118 can include slots, grooves, clips, or other structures to engage at least a portion, if not the entirety, of the first end of the expandable prosthesis. For example, the inner retention member 118 may be used to engage tabs on the longitudinal struts 12 of the prosthesis 10 illustrated in FIG. 1A of U.S. application Ser. No. 14/197,690. In some embodiments, the inner retention assembly 116 can include an outer retention shaft 119 to which an outer retention member 120, such as an outer retention ring, can be attached at a distal end of the outer retention shaft 119.

As shown in the illustrated embodiment, the inner retention member 118 and the outer retention member 120 can be moveable relative to each other and can cooperate to release the expandable prosthesis from the inner retention assembly 116. For example, the outer retention member 120 can be sized and shaped to cover the inner retention member 118 when the first end of the expandable prosthesis is engaged with the inner retention member 118. In this embodiment, the inner retention shaft 117 may be hollow so that the outer retention shaft 119 is slidable within the inner retention shaft 117. In embodiments where the expandable prosthesis is engaged with the inner retention member 118, use of the outer retention member 120 over the inner retention member 118 can restrain the expandable prosthesis from expanding radially outward from the longitudinal axis of the prosthesis. Upon movement of the outer retention member 120 relatively away from the inner retention member 118, the inner retention member 118 can be uncovered such that the expandable prosthesis can expand radially outward from the longitudinal axis of the prosthesis. In some embodiments, release of the first end of the expandable prosthesis from the inner retention assembly 116 wholly releases the expandable prosthesis from the delivery system 100. Further details of an inner retention assembly are found in U.S. Pat. No. 8,652,203 referenced above. With continued reference to the embodiment shown in FIG. 1, the outer elongate hollow member 110 can be sized and shaped such that, when the expandable prosthesis is mounted on the inner retention assembly 116 and/or the inner retention shaft 117, the outer elongate hollow member 110 covers both the first and second ends of the expandable prosthesis to hold the prosthesis in a radially restrained configuration. The outer elongate hollow member 110 can be sized and shaped to be slidable over the inner retention assembly 116. With respect to the arrangement shown in FIG. 1, when the first end of a prosthesis is mounted on the inner retention assembly 116 and the second end of the prosthesis is positioned proximally of the first end, the outer elongate hollow member 110 would be moved proximally relative to the inner retention assembly 116 so that the inner retention assembly 116 and the prosthesis are covered by the outer elongate hollow member 110. The outer elongate hollow member 110 may comprise a flexible plastic material, and in some embodiments may be slitted at its proximal end to facilitate moving the outer elongate hollow member 110 over the prosthesis when the prosthesis is loaded onto the delivery system. The outer elongate hollow member 110 may comprise structures and/or materials that are generally resistant to radial expansion while being generally compliant to radial collapse.

With the inner retention assembly 116 and the prosthesis covered by the outer elongate hollow member 110, the outer elongate hollow member 110 can be designed such that the outer elongate hollow member 110 can slide distally relative to the inner retention assembly 116 and/or the inner retention assembly 116 can slide proximally relative to the outer elongate hollow member 110. In some embodiments, distal movement of the outer elongate hollow member 110 relative to the inner retention assembly 116 can uncover at least the second end of the expandable prosthesis when the expandable prosthesis is mounted on the inner retention assembly 116. Distal movement of the outer elongate hollow member 110 relative to the inner retention assembly 116 and/or receiving member 112 can cause longitudinal compression or collapse of at least a portion of the outer elongate hollow member 110 into the receiving member 112. Accordingly, it should be understood that in some embodiments the outer elongate hollow member 110, or at least some portion thereof such as a proximal portion, can be formed from a generally deformable material. For example, the outer elongate hollow member 110 can be a collapsible polymer sheath.

With reference now to the embodiment shown in FIGS. 2-5 which illustrates a delivery device or system 200, the delivery system 200 can include components, structures, features and/or functionality which are the same as, or similar to, those described in connection with any of the delivery systems described herein such as delivery system 100. The delivery system 200 can include a plurality of sheaths and/or shafts which can be sized and shaped to be slidable relative to each other. Accordingly, it should be understood that one or more of the plurality of shafts can be concentric with respect to another of the shafts to facilitate slidable movement of the shafts relative to each other. The plurality of shafts can be coupled to one or more other components of the delivery system 200.

Figure 2:
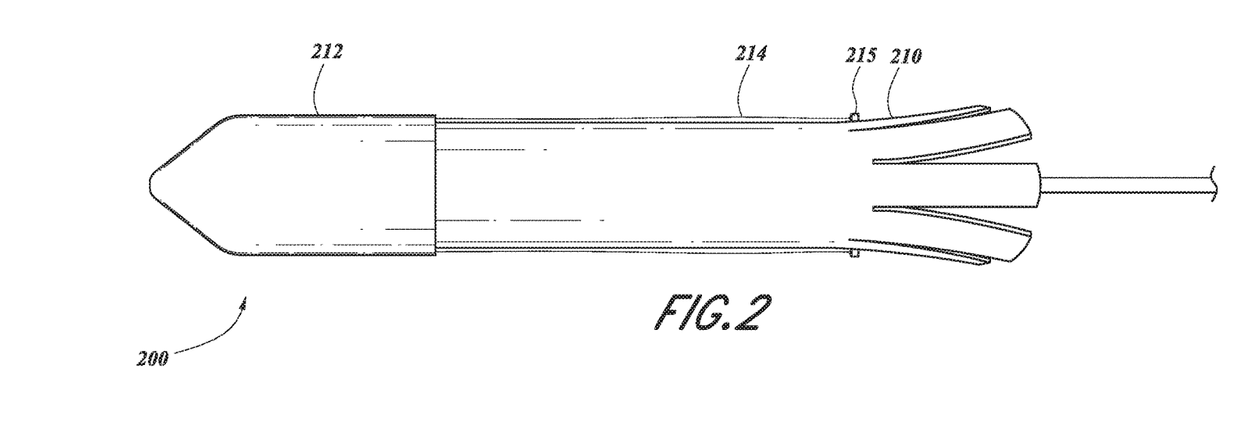
FIG. 2 shows a side elevation view another embodiment of a delivery system having pull wires in a first state.

With reference first to the embodiment of FIG. 2 which illustrates a side elevation view of the delivery system 200, the delivery system 200 can include an outer elongate hollow member 210 such as a sheath, a receiving member 212, and one or more pull wires 214. Similar to outer elongate hollow member 110, the outer elongate hollow member 210 can have a proximal and distal end, with the receiving member 212 positioned around the distal end of the outer elongate hollow member 210. The one or more pull wires 214 can be attached to at least a portion of the outer elongate hollow member 210. As shown in the illustrated embodiment, the one or more pull wires can be attached to one or more corresponding connector mechanisms 215 attached along a proximal portion of the outer elongate hollow member 210. In some embodiments, connector mechanism 215 can be a clip, suture, or fastener or other mechanical fastener as desired. In some embodiments, connector mechanism 215 can be a bonding agent such as an adhesive or weld directly formed on the outer elongate hollow member 210. Connector mechanisms 215 can be formed from a material different from that of the outer elongate hollow member 210 or can be formed from the same material. In some embodiments, the one or more pull wires 214 are integral with the outer elongate hollow member 210.

Figure 3:
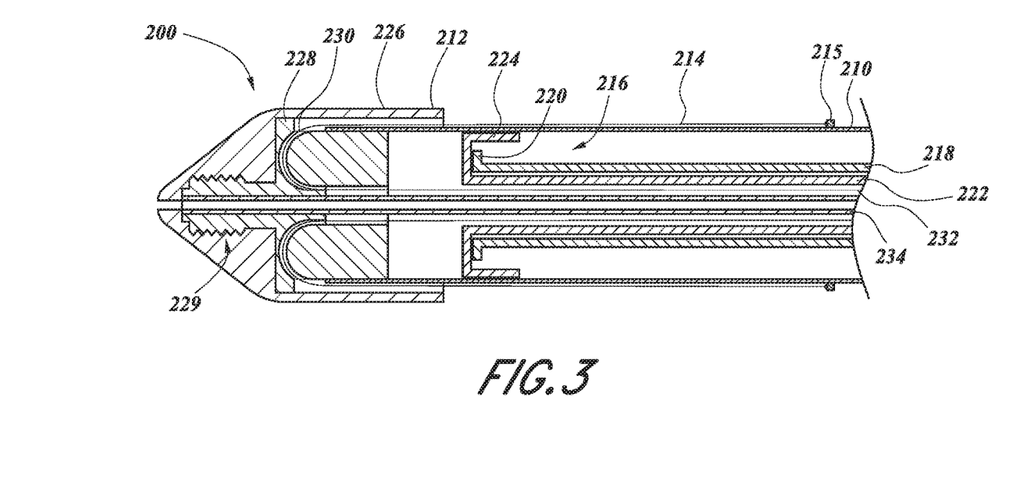
FIG. 3 illustrates a partial, cross-sectional view of the delivery system of FIG. 2.

With reference now to the embodiment shown in FIG. 3 which illustrates a partial cross-sectional view of the delivery system 200, an inner retention assembly 216 of the delivery system 200 is more clearly illustrated. Similar to inner retention assembly 116, inner retention assembly 216 can be designed to carry an expandable prosthesis to an in situ target location. The inner retention assembly 216 can radially restrain a first end of the expandable prosthesis when the expandable prosthesis is mounted thereon with a second end of the expandable prosthesis extending proximally therefrom.

As shown in the illustrated embodiment, the inner retention assembly 216 can include an inner retention shaft 218, having a proximal and distal end, over which the expandable prosthesis can be mounted. An inner retention member 220, such as an inner retention ring, can be attached to a distal end of the inner retention shaft 218. In some embodiments, the inner retention shaft 218 and inner retention member 220 can form a monolithic unit. In other embodiments, the inner retention shaft 218 and inner retention member 220 can be separate components which can be attached after manufacture. The inner retention assembly 216 can include an outer retention shaft 222 having a proximal end and a distal end to which an outer retention member 224, such as an outer retention ring, can be attached. The inner retention member 220 and the outer retention member 224 can be moveable relative to each other and can cooperate to release the expandable prosthesis from the inner retention assembly 216. For example, as shown in the illustrated embodiment, the outer retention member 224 can be sized and shaped to cover the inner retention member 220 when the first end of the expandable prosthesis is engaged with the inner retention member 220. Upon movement of the outer retention member 224 relatively away from the inner retention member 220, the inner retention member 220 can be uncovered such that the expandable prosthesis can expand radially outward from the longitudinal axis of the prosthesis. In some embodiments, release of the first end of the expandable prosthesis from the inner retention assembly 216 wholly releases the expandable prosthesis from the delivery system 200.

With continued reference to the embodiment shown in FIG. 3, the inner retention member 220 and the outer retention member 224 can be moved relative to each other via moving either the inner retention shaft 218 relative to the outer retention shaft 222 or by moving the outer retention shaft 222 relative to the inner retention shaft 218. Accordingly, the outer retention shaft 222 can be sized and shaped to be slidable relative to the inner retention shaft 218. For example, as shown in the illustrated embodiment, the outer retention shaft 222 can be sized to be slidable within the inner retention shaft 218.

Figure 4:
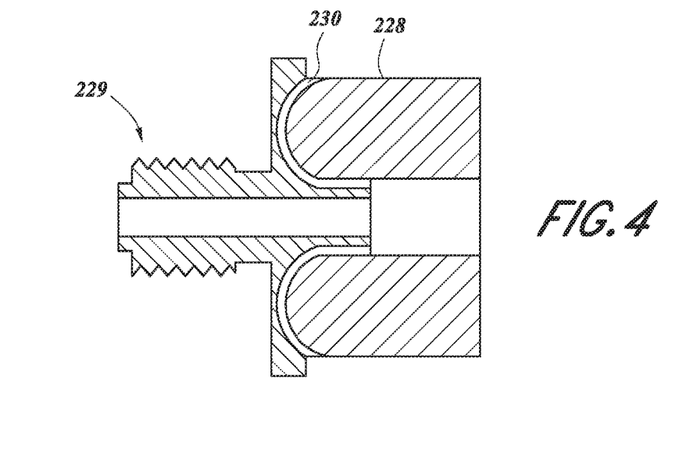
FIG. 4 illustrates a partial cross-sectional view of an insert of the delivery system of FIG. 2
Figure 5:
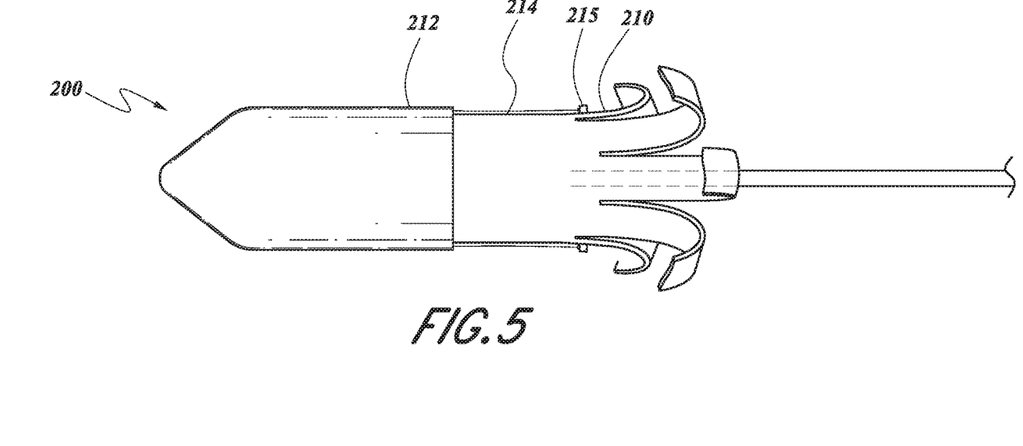
FIG. 5 illustrates the delivery system of FIG. 2 in a second state.

With continued reference to the embodiment shown in FIGS. 3 and 4, the receiving member 212 can include a nose cone 226 and an insert 228. The insert 228 can engage the nose cone 226 via a threaded end 229 as illustrated or via any other suitable mechanism such as a snap-fit connection, clips, separate fasteners such as screws, bolts, rivets and the like, bonding agents such as an adhesive, welds or other bonding techniques, any other attachment mechanism or technique as desired, or any combination of these mechanisms and techniques. The insert 228 can include a path 230 through which the one or more pull wires 224 can be inserted and guided. The path 230 can be curved and, in some embodiments, have a "U" shape. As shown in the illustrated embodiment, the one or more pull wires 224 can extend from the corresponding connector mechanisms 215, pass through the path 230 of the receiving member 212 and pass through and out of the inner retention assembly 216. Accordingly, proximal movement of the end 232 of the one or more pull wires 224 can result in distal movement of the end of the one or more pull wires 224 attached to corresponding connector mechanisms 215. As a result, retraction of the end 232 of pull wire 224 in a proximal direction can cause the proximal portion of the outer elongate hollow member 210 to be moved distally and relatively toward the receiving member 212 to which the outer elongate hollow member 210 is attached. As shown in the embodiment of FIG. 5, the outer elongate hollow member 210 can longitudinally compress or collapsed into the receiving member 212.

With reference back to the embodiment shown in FIG. 3, the delivery system 200 can include a nose cone shaft 234 having a proximal and distal end. The nose cone 226 and/or insert 228 can be attached to a distal end of the nose cone shaft 234. The nose cone shaft 234 can be sized and shaped to be moveable relative to the inner retention assembly 216. For example, as shown in the illustrated embodiment, the nose cone shaft 234 can be sized and shaped to be slidable within the outer retention shaft 222. The nose cone shaft 234 can also be sized and shaped to allow a guidewire to pass therethrough.

With reference now to the embodiment shown in FIGS. 6-13 which illustrates a delivery device or system 300, the delivery system 300 can include components, structures, features and/or functionality which are the same as, or similar to, those described in connection with any of the delivery systems described herein such as delivery systems 100, 200. The delivery system 300 can include a plurality of sheaths and/or shafts which can be sized and shaped to be slidable relative to each other. Accordingly, it should be understood that one or more of the plurality of shafts can be concentric with respect to another of the shafts to facilitate slidable movement of the shafts relative to each other. The plurality of shafts can be coupled to one or more other components of the delivery system 300.

Figure 6:
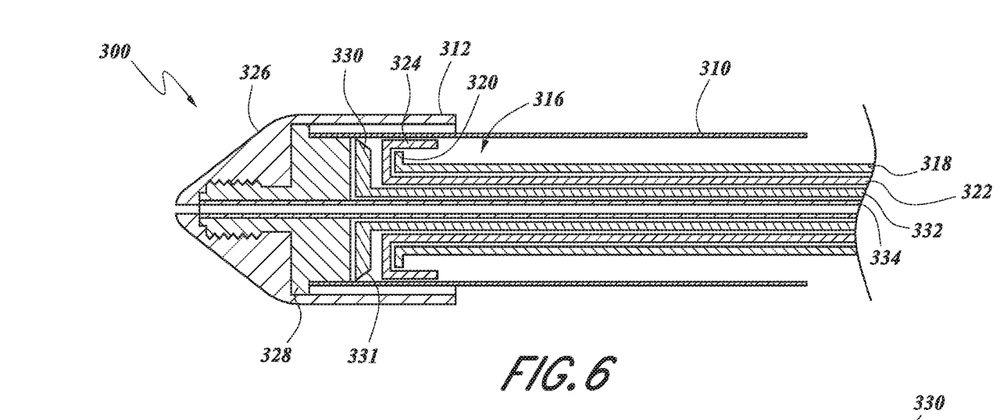
FIG. 6 shows another embodiment of a delivery system having a compression member.

With reference first to the embodiment of FIG. 6, the delivery system 300 can include an outer elongate hollow member 310 such as a sheath and a receiving member 312. Similar to outer elongate hollow member 210, the outer elongate hollow member 310 can have a proximal and distal end, with the receiving member 312 positioned around the distal end of the outer elongate hollow member 310. Similar to delivery system 200, the delivery system 300 can include an inner retention assembly 316 which can be designed to carry an expandable prosthesis to an in situ target location. The inner retention assembly 316 can radially restrain a first end of the expandable prosthesis when the expandable prosthesis is mounted thereon with a second end of the expandable prosthesis extending proximally therefrom.

As shown in the illustrated embodiment, the inner retention assembly 316 can include an inner retention shaft 318, an inner retention member 320, an outer retention shaft 322 and an outer retention member 324 which can have structures, features and/or functionality which are the same as, or similar to, those of inner retention shaft 218, inner retention member 220, outer retention shaft 222 and outer retention member 224 respectively. Moreover, the receiving member 312 can include a nose cone 326, an insert 328, and a nose cone shaft 324. Nose cone 326, insert 328 and nose cone shaft 334 can have structures, features and/or functionality which are the same as, or similar to, those of nose cone 226, insert 228, and nose cone shaft 334 respectively. For purposes of brevity, reference should be made to the discussion of these components above in connection with FIGS. 2-5. As shown in the illustrated embodiment, insert 328 does not include a guide path.

Figure 7:
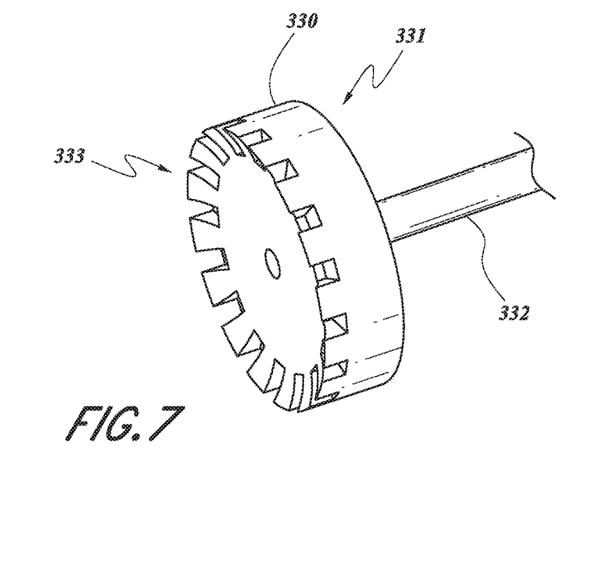
FIG. 7 illustrates a perspective view of a compression member and compression shaft of the delivery system of FIG. 6.

With continued reference to the embodiment shown in FIGS. 6 and 7, delivery system 300 can include a compression member 330, such as a squash plate, designed to compress or collapse the outer elongate hollow member 310. The compression member 330 can have a tapered or non-tapered proximal side 331 and a toothed distal side 333 having a plurality of slots or teeth for engaging an inner surface the outer elongate hollow member 310. The compression member 330 can be attached to the distal end of a compression shaft 332. The compression member 330 can be moveable relative to the inner retention assembly 316 and/or receiving member 312 to compress or collapse the outer elongate hollow member 310. As shown in the illustrated embodiment, the compression member 330 can be moved relative to the inner retention assembly 316 and/or the receiving member 312 via movement of one or more of the inner retention shaft 318, outer retention shaft 322, and nose cone shaft 334 relative to the compression shaft 332. As shown in the illustrated embodiment, the compression shaft 332 can be sized and shaped to be slidable within the inner retention assembly 316.

The embodiment of FIGS. 8-13 illustrates steps of a method of operating the delivery system 300 and releasing a prosthesis, such as an intralumenal frame assembly, to intralumenal tissue at an in situ target location. The steps of this method can be carried out while the prosthesis is in a radially compacted state within the delivery system 300. In some embodiments, the longitudinal axis of the prosthesis, which runs between the first and second ends of the prosthesis, can be parallel to and/or concentric with the longitudinal axis of one or more shafts of the delivery system 300. The steps of this method can be used to transapically deliver a replacement heart valve to a mitral valve location.

Figure 8:
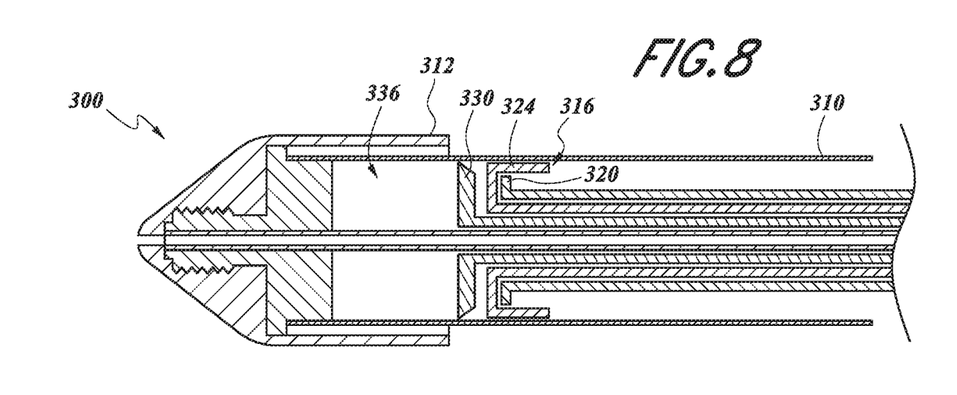
FIGS. 8-13 illustrate steps of a deployment method using the delivery system of FIG. 6.

With reference first to the step of FIG. 8, the delivery system 300 is shown with the receiving member 312, the inner retention assembly 316, and the compression member 330 in a second configuration. In this second configuration, the inner retention assembly 316 and compression member 330 are spaced away from the receiving member 312 such that a gap 336 is formed between the compression member 330 and the receiving member 312. These components can be transitioned from the first configuration illustrated in FIG. 6 to the second configuration illustrated in FIG. 8 via movement of the compression member 330 and the inner retention assembly 316 relatively away from the receiving member 312. For example, the receiving member 312 can be advanced distally relative to the compression member 330 and the inner retention assembly 316. Likewise, the compression member 330 and the inner retention assembly 316 can be retracted proximally relative to the receiving member 312. Either of these movements may cause a prosthesis within the outer elongate hollow member 310 to become at least partially uncovered. For example, a second end of a prosthesis may be uncovered and be allowed to radially expand due to either of these movements, with the first end of the prosthesis still restrained by the inner retention assembly 316.

Figure 9:
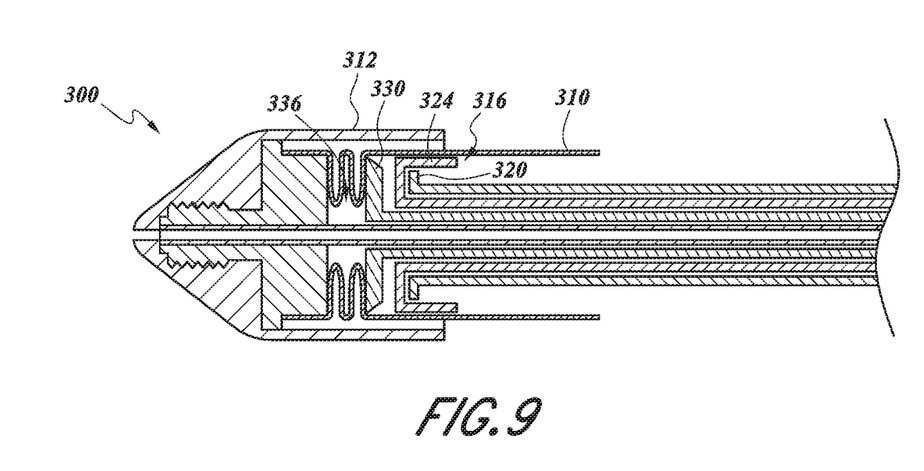

With reference next to the step of FIG. 9, the delivery system 300 is shown with the receiving member 312, the inner retention assembly 316, and the compression member 330 back in the first configuration. These components can be transitioned from the second configuration back to the first configuration via movement of the compression member 330 and the inner retention assembly 316 relatively toward the receiving member 312. For example, the receiving member 312 can be retracted proximally relative to the compression member 330 and the inner retention assembly 316. Likewise, the compression member 330 and the inner retention assembly 316 can be advanced distally relative to the receiving member 312.

As a result of this relative movement of the compression member 330 and the inner retention assembly 316 towards the receiving member 312, the outer elongate hollow member 310 is moved relatively toward the receiving member 312. Without being limited to a particular theory of operation, this movement can result from frictional engagement between the compression member 330 and/or the inner retention assembly 316 with the outer elongate hollow member 310. As a result of movement of the outer elongate hollow member 310, the outer elongate hollow member 310 can be compressed or collapsed into the gap 336 between the receiving member 312 and the compression member 330. As shown in the illustrated embodiment, the outer elongate hollow member 310 has slightly folded within this gap 336. Once the movement illustrated in FIG. 9 has been achieved, a prosthesis covered by the outer elongate hollow member 310 may be further exposed and may further radially expand.

Figure 10:
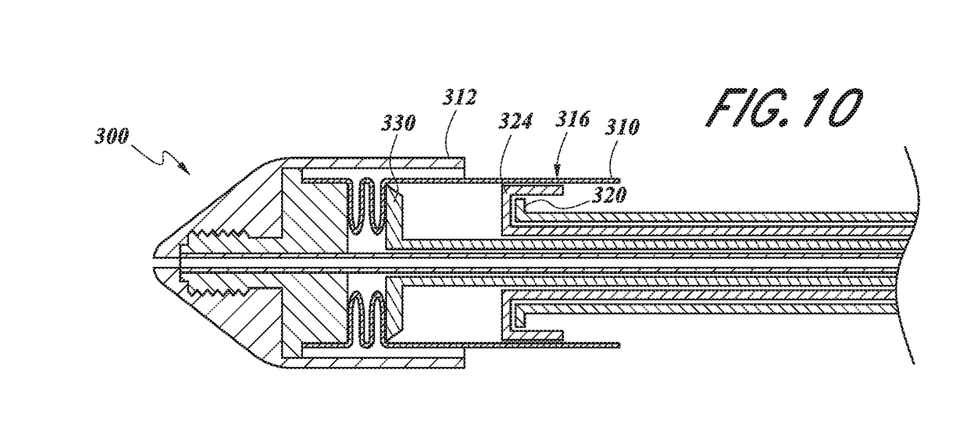

With reference next to the step of FIG. 10, the delivery system 300 is shown with the receiving member 312, the inner retention assembly 316, and the compression member 330 in a third configuration. These components can be transitioned from the first configuration to the third configuration via movement of the inner retention assembly 316 relatively away from the receiving member 312 while maintaining the compression member 330 generally in the same position relative to the receiving member 312. For example, the receiving member 312 and compression member 330 can be advanced distally relative to the inner retention assembly 316. Likewise, the inner retention assembly 316 can be retracted proximally relative to the receiving member 312 and the compression member 330. Either of these movements may further uncover the prosthesis and permit it to radially expand.

Due to the compression member 330 remaining in contact with folds of the outer elongate hollow member 310, the outer elongate hollow member 310 remains generally in the same compressed or collapsed configuration as the inner retention assembly 316 is moved relatively away from the receiving member 312. Accordingly, it should be noted that the outer elongate hollow member 310 remains in generally the same compressed or collapsed state as when the components were in the previous configuration (as shown in FIG. 9).

Figure 11:
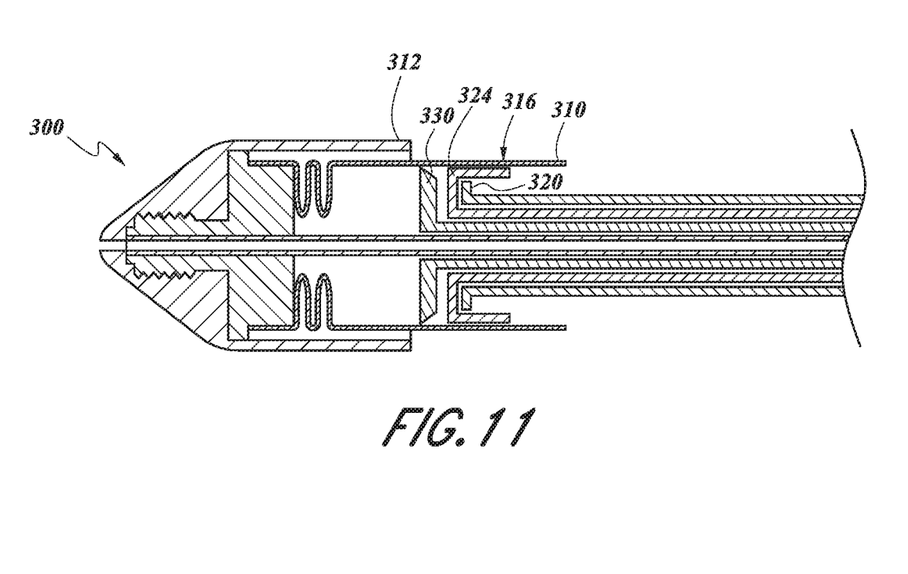

With reference next to the step of FIG. 11, the delivery system 300 is shown with the receiving member 312, the inner retention assembly 316, and the compression member 330 back in the second configuration. These components can be transitioned from the third configuration back to the second configuration via movement of the compression member 330 relatively away from the receiving member 312 while maintaining the inner retention assembly 316 generally in the same position relative to the receiving member 312. For example, the compression member 330 can be retracted proximally relative to the receiving member 312 and the inner retention assembly 316. Likewise, the receiving member 312 and the inner retention assembly 316 can be advanced distally relative to the compression member 330.

Due in part to the tapered shape of the compression member 330 on the proximal side and contact between the inner retention assembly 316 and the outer elongate hollow member 310, the outer elongate hollow member 310 remains generally in the same compressed or collapsed configuration as when the components were in the previous configurations (as shown in FIGS. 9 and 10). It should be noted that while the receiving member 312, the inner retention assembly 316 and the compression member 330 are in a similar position to that shown in FIG. 8, movement of these components from the second configuration to the first configuration, from the first configuration to the third configuration, and from the third configuration back to the second configuration causes compression or collapse of the outer elongate hollow member 310. This procedure can be repeated until the outer elongate hollow member 310 has been moved sufficiently toward the receiving member 312 to expose at least a portion, if not the entirety, of the prosthesis contained on the delivery system 300. In order to facilitate compression or collapse of the outer elongate hollow member 310, the outer elongate hollow member 310 can be manufactured from a material and/or have a structure with reduced column strength.

Figure 12:
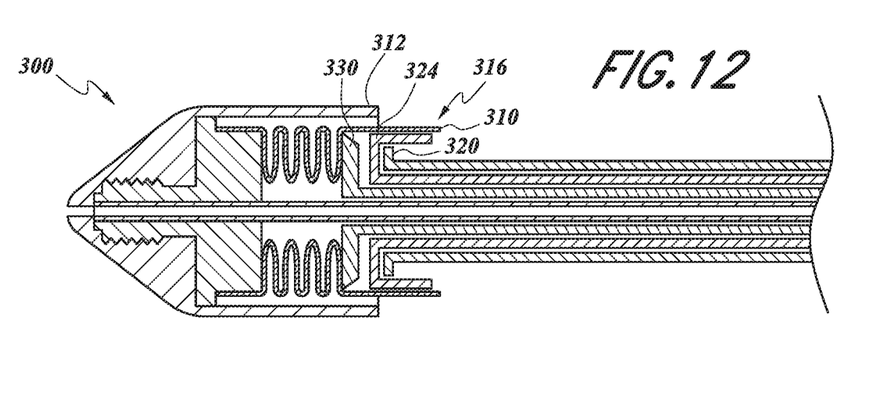
Figure 13:
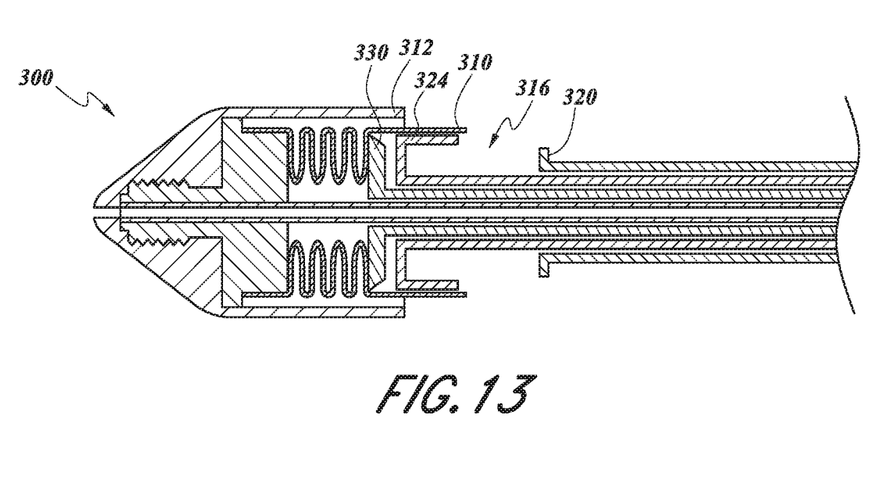

With reference next to the step of FIG. 12, the delivery device 300 is shown in the second configuration with the outer elongate hollow member 310 having been moved sufficiently towards the receiving member 312. At this point, the prosthesis may be entirely or almost entirely uncovered other than its first end being retained by the inner retention assembly 316. With reference next to the step of FIG. 13, the inner retention assembly 316 can be actuated to release the prosthesis from the delivery system 300. As shown in the illustrated embodiment, release of the prosthesis can be achieved by moving the inner retention member 320 relatively away from the outer retention member 324.

It will be understood that the delivery devices, such as delivery devices 100, 200, 300, can include many additional features similar to those described in U.S. Pat. Nos. 8,414,644 and 8,652,203, the entirety of each of which is hereby incorporated by reference and made a part of this specification. For example, the nose cone can include a prosthesis retention mechanism such as an inner retention ring that can be used to engage with the prosthesis as may be described in these applications. Struts or other parts of a prosthesis can be engaged with the inner retention ring and the nose cone can cover both the prosthesis and the inner retention ring to secure the prosthesis on the delivery devices 100, 200, 300. In addition, the delivery device can be used in delivery methods similar to those described in the above referenced patents and application.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A delivery system for controlled deployment of an expandable prosthesis, the delivery system comprising:
    an inner retention assembly comprising an inner elongate member having a proximal end and a distal end configured to carry the expandable prosthesis to an in situ target location, wherein the inner retention assembly is configured to radially restrain a first end of the expandable prosthesis when the expandable prosthesis is mounted over the inner elongate member with the second end of the expandable prosthesis positioned proximally of the first end;
    an outer elongate hollow member having a proximal end and a distal end that is slidable over the inner retention assembly, the outer elongate hollow member configured to cover the first and second ends of the expandable prosthesis when the expandable prosthesis is mounted over the inner elongate member; and
    a receiving member provided at the distal end of the outer elongate hollow member, wherein the distal end of the outer elongate hollow member is positioned within the receiving member and the proximal end of the outer elongate hollow member is spaced proximally away from the receiving member;
    wherein the outer elongate hollow member is moveable in a distal direction relative to the inner retention assembly to uncover at least the second end of the expandable prosthesis when the expandable prosthesis is mounted over the inner elongate member, wherein distal movement of the outer elongate hollow member relative to the inner retention assembly causes longitudinal collapse of at least a portion of the outer elongate hollow member into the receiving member.

2. The delivery system of claim 1, wherein the inner retention assembly comprises an inner retention ring at the distal end of the inner elongate member configured to engage the first end of the expandable prosthesis.

3. The delivery system of claim 2, wherein the inner retention assembly further comprises an outer retention ring configured to cover the inner retention ring when the inner retention ring engages the first end of the expandable prosthesis.

4. The delivery system of claim 1, wherein the receiving member comprises a nose cone.

5. The delivery system of claim 4, further comprising a nose cone shaft slidable within the inner elongate member, wherein the nose cone is connected to a distal end of the nose cone shaft.

6. The delivery system of claim 1, further comprising a plurality of pull wires connected to a proximal portion of the outer member and configured pull the outer member distally into the receiving member.

7. The delivery system of claim 6, wherein the pull wires extend through a curved path within the receiving member.

8. The delivery system of claim 1, further comprising a squash plate configured to cause longitudinal collapse of the outer member.

9. The delivery system of claim 8, further comprising a compression shaft slidable within the inner retention assembly, wherein the squash plate is connected to a distal end of the compression shaft.

10. The delivery system of claim 1, wherein the outer elongate hollow member comprises a collapsible polymer sheath.

11. The delivery system of claim 1, further comprising an expandable prosthesis having a first end radially restrained by the inner retention assembly and wherein the first end and the second end of the expandable prosthesis are covered by the outer elongate hollow member.

\* \* \* \* \*